United States Patent [19]

Stewart

[11] 4,243,155
[45] * Jan. 6, 1981

[54] VALVING AND AUTOMATIC PRESSURE REGULATOR FOR INHALATION APPARATUS

[75] Inventor: Maurice M. Stewart, West Bloomfield, Mich.

[73] Assignee: Oxygen Therapy Institute, Inc., Oak Park, Mich.

[ * ] Notice: The portion of the term of this patent subsequent to Aug. 29, 1995, has been disclaimed.

[21] Appl. No.: 43,748

[22] Filed: May 29, 1979

Related U.S. Application Data

[63] Continuation of Ser. No. 900,916, Apr. 28, 1978, abandoned, which is a continuation of Ser. No. 761,802, Jan. 24, 1977, Pat. No. 4,109,828.

[51] Int. Cl.³ .............................................. B67D 5/22
[52] U.S. Cl. .................................. 222/3; 128/204.18; 128/205.24; 222/44
[58] Field of Search ..................... 222/3, 44, 130, 182, 222/183, 396, 397; 128/142 R, 145.8, 185, 203; 137/505.11, 613; 138/45 A, 46; 403/119, 152, 154, 155, 161–163, 315, 316, 399

[56] References Cited

U.S. PATENT DOCUMENTS

| | | | |
|---|---|---|---|
| 1,142,177 | 6/1915 | Kennedy | 403/154 |
| 1,494,395 | 5/1924 | Wells | 137/625.19 |
| 1,569,311 | 1/1926 | Barstow | 403/154 X |
| 2,468,483 | 4/1949 | Chambers et al. | 222/3 X |
| 2,831,607 | 4/1958 | Berndt | 222/3 |
| 3,547,143 | 12/1970 | Mills, Jr. | 137/505.42 X |
| 3,693,653 | 9/1972 | Cramer et al. | 137/613 X |
| 4,088,131 | 5/1978 | Elam | 128/145.8 X |
| 4,109,828 | 8/1978 | Stewart | 222/3 |

Primary Examiner—Robert J. Spar
Assistant Examiner—Fred A. Silverberg
Attorney, Agent, or Firm—Barnes, Kisselle, Raisch & Choate

[57] ABSTRACT

An inhalation apparatus comprising an automatic pressure regulator including a body having an opening for receiving the valve of an oxygen tank and an outlet for a hose extending from the outlet. A valve is attached to the hose and includes a manual control for selectively varying the volume of oxygen passing through the hose to an inhaling mask on the end of the hose. The pressure regulator body includes two chambers, a passage extending from one chamber to the other, and an inlet passage extending to one chamber. Each chamber has a diaphragm closing one wall thereof and a spring yieldingly urging the diaphragm in one direction. An orifice is associated with the inlet and an orifice is associated with the passage. A lever is pivoted adjacent its respective diaphragm and has one end thereof pivotally connected to its respective diaphragm and the other end thereof engaging a valve associated with the respective orifice. The lever is pivoted to the body by a pin extending through the lever and engaging recesses. Headed screws are threaded into the body to hold the pin in the recesses. A hose extends from the regulator and a manually controlled regulator valve is provided to selectively control the flow of oxygen from the regulator.

8 Claims, 10 Drawing Figures

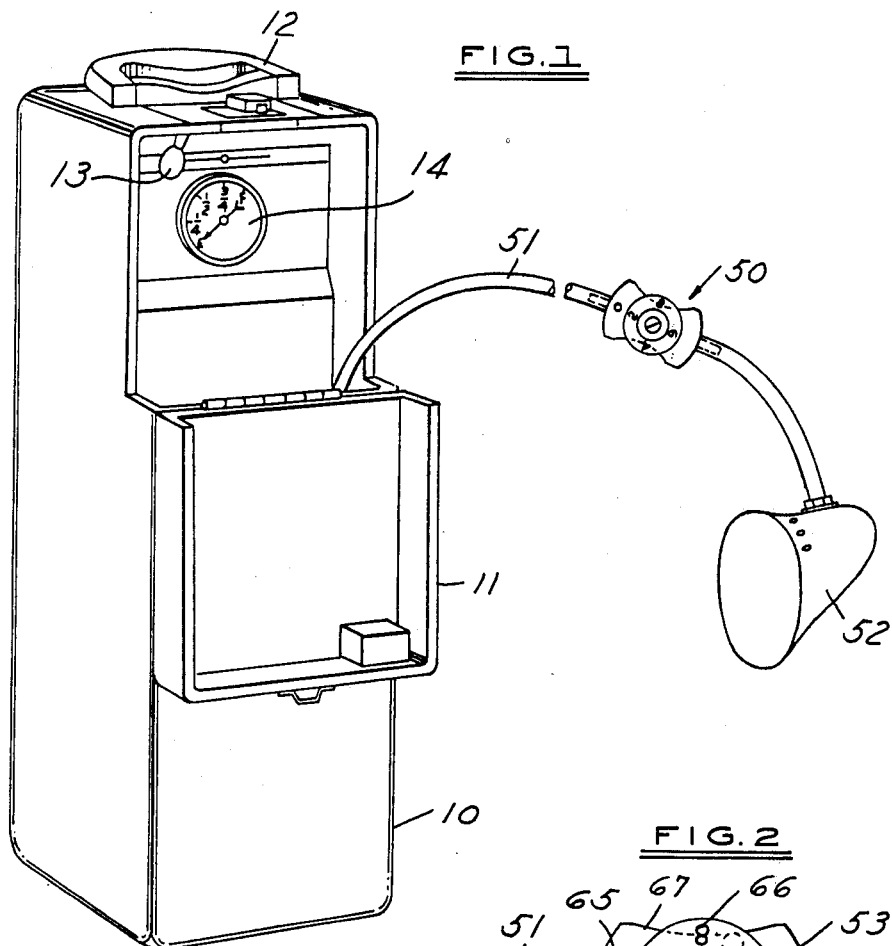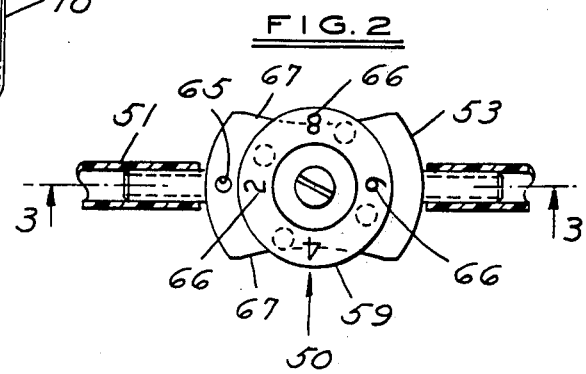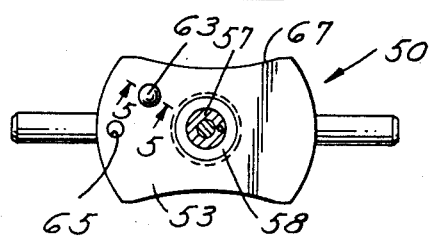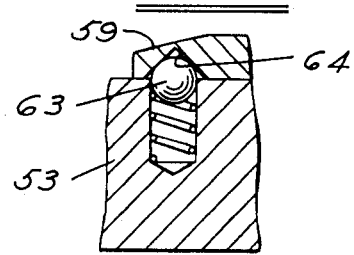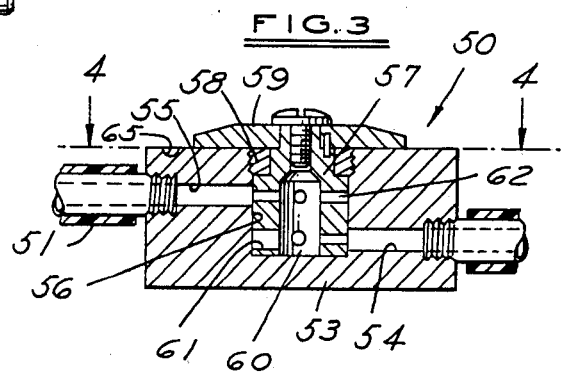

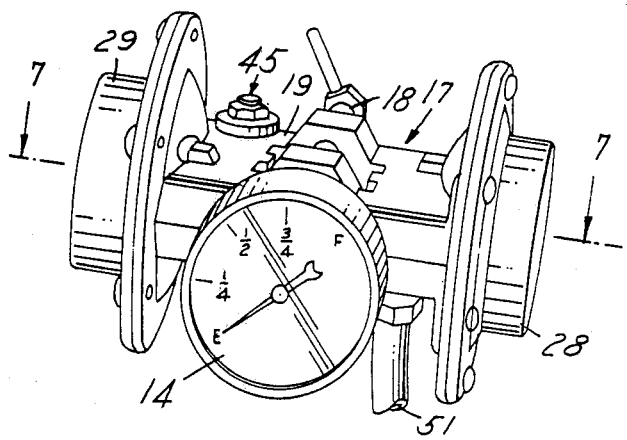
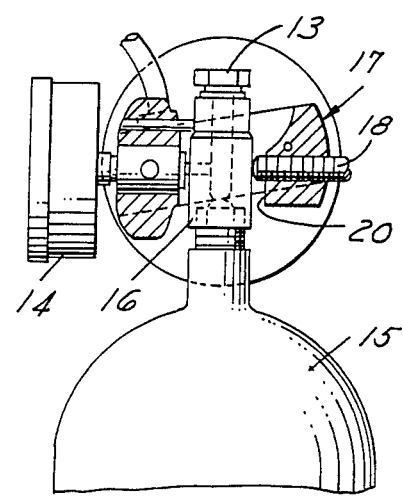
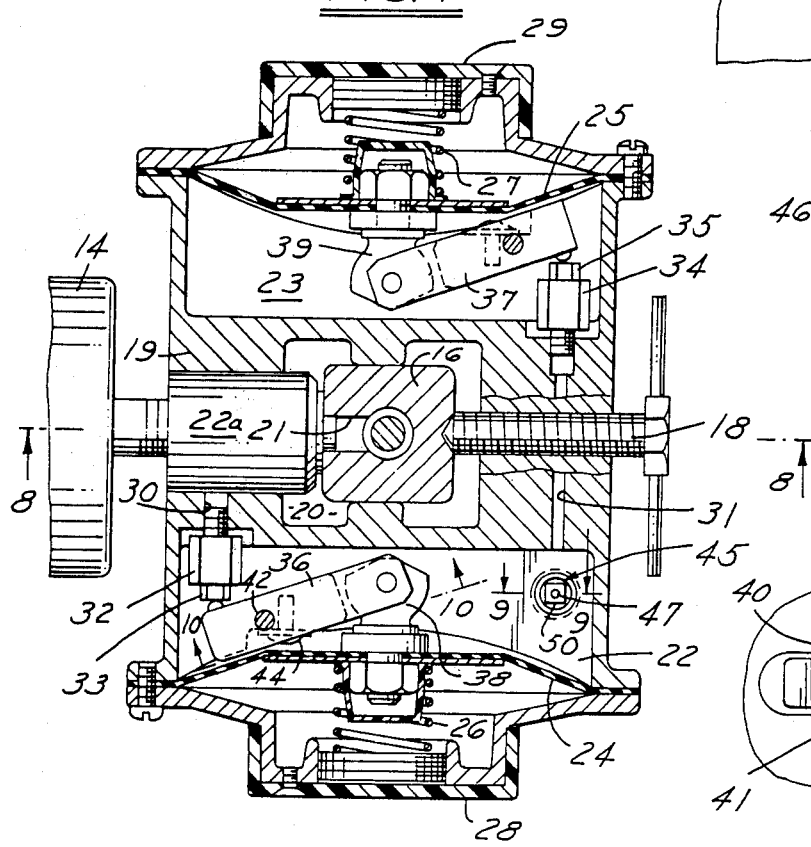
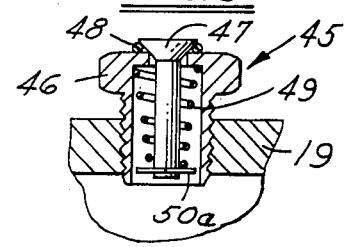
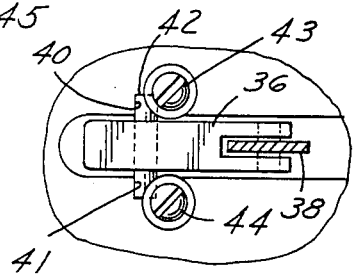

VALVING AND AUTOMATIC PRESSURE REGULATOR FOR INHALATION APPARATUS

This application is a continuation of application Ser. No. 900,916, filed Apr. 28, 1978, now abandoned, which is a continuing application of application Ser. No. 761,802, filed Jan. 24, 1977, now U.S. Pat. No. 4,109,828.

This invention relates to inhalation apparatus and particularly to portable inhalation apparatus adapted to be used for providing oxygen to patients.

BACKGROUND AND SUMMARY OF THE INVENTION

A common type of portable oxygen apparatus is disclosed in U.S. Pat. No. 2,831,607 and comprises an automatic pressure regulator which is mounted on the outlet valve of an oxygen tank and is adapted to provide oxygen to a patient.

As shown in such patent, the automatic pressure regulator comprises a body which has a pair of chambers each having an orifice associated therewith with one chamber communicating with the other and a diaphragm associated with each orifice to control the pressure of oxygen in each chamber. The oxygen passes in the first chamber and thereafter into the second chamber before passing to the patient.

Such an inhalation apparatus has proved quite successful in providing oxygen as required.

As disclosed in U.S. Pat. No. 2,831,607, it is desirable to provide for a safety escape for the gas and as disclosed in the patent, a safety valve is associated with the diaphragm in the second chamber.

Among the objectives of the present invention are to provide a safety relief that is reliable and will continue to provide oxygen to the patient even if the pressure exceeds a predetermined amount. Furthermore, in accordance with the invention, the automatic regulator provides a predetermined amount of oxygen. Among the further objectives of the present invention are to provide an inhalation apparatus which can be more readily serviced.

DESCRIPTION OF THE DRAWINGS

FIG. 1 is a perspective view of an apparatus embodying the invention.

FIG. 2 is a fragmentary plan view on an enlarged scale of a portion of the apparatus shown in FIG. 1.

FIG. 3 is a sectional view taken along the line 3—3 in FIG. 2.

FIG. 4 is a sectional view taken along the line 4—4 in FIG. 3.

FIG. 5 is a fragmentary sectional view on an enlarged scale taken along the line 5—5 in FIG. 4.

FIG. 6 is a perspective view of the automatic pressure regulator embodying the invention.

FIG. 7 is a longitudinal sectional view taken along the line 7—7 in FIG. 6.

FIG. 8 is a vertical sectional view taken along the line 8—8 in FIG. 7 on the reduced scale.

FIG. 9 is a fragmentary sectional view on an enlarged scale taken along the line 9—9 in FIG. 7.

FIG. 10 is a fragmentary sectional view taken along the line 10—10 in FIG. 7.

DESCRIPTION

Referring to FIG. 1, the invention relates to a portable inhalation apparatus which comprises a case 10 that includes a pivoted cover 11 and a carrying handle 12. When the cover is open, a lever 13 provides an on-off control for the oxygen and a pressure gauge 14 indicating the amount of oxygen remaining is visible. This general construction is shown in the aforementioned U.S. Pat. No. 2,831,607.

Referring to FIG. 8, an oxygen tank 15 is provided within the case 10 and has an on-off valve 16 controlled by lever 13. A pressure regulator 17 is mounted on the valve 16 by a screw 18.

The pressure regulator 17 includes a body 19 that has an opening 20 therethrough into which the valve 16 extends. The screw 18 holds the regulator body 19 against the valve 16 so that the outlet passage 21 of valve 16 is aligned with the connector 22a that also supports the gauge 14. The regulator body 19 is formed with two chambers 22, 23 each of which has an open end closed by a diaphragm 24, 25 that is yieldingly urged inwardly by springs 26, 27 interposed between a cap 28, 29 respectively, and the respective diaphragm.

The body 19 of the regulator further includes an inlet passage 30 extending from the connector 22a to the first chamber 22 and a connecting passage 31 that extends from the first chamber 22 to the second chamber 23. A variable orifice 32 is provided between the inlet 30 and the chamber 22 and is controlled by a member 33. Similarly a variable orifice 34 with a member 35 is provided in the passage 31.

A lever 36, 37 is associated with each diaphragm 24, 25 and has one end thereof pivoted to a pivot member 38, 39 and the other end thereof adapted to engage the orifice member 33, 35 respectively.

Each lever 36, 37 is pivoted intermediate its ends to the body 19 by an identical structure such as shown in FIG. 10 which includes groove shaped recesses 40, 41 that receive a pin 42 that passes through the lever 36. The pin 42 is held in the recesses 40, 41 by cap screws 43, 44. In this fashion, the regulator can be readily serviced to replace the diaphragm or other mechanism merely by removing the cap screws.

Further in accordance with the invention a pressure relief valve 45 is provided from the first chamber 22 to the atmosphere. As shown in FIG. 9, the pressure relief valve 45 includes a body 46 and a valve member 47 having an O-ring 48 thereon. The end of the valve member 47 is frusto-conical and the valve member is yieldingly urged against the O-ring 48 by a spring 49 interposed between a washer 50a and the body 46.

When the pressure in chamber 22 exceeds a predetermined value, the valve 45 functions to relieve the pressure in the first chamber, reducing it to a safe value but at the same time continuing to maintain the pressure in chamber 22 and in turn in chamber 23 so that the supply of oxygen to the patient continues.

Referring to FIGS. 1-5, it has been found that the amount of oxygen supplied to a patient, for example, in transporting the patient from one position to another in a hospital or for use in the home varies in accordance with the condition of the patient so that one patient can receive more or less than another. In order to provide a ready control of the volume to each patient, a manually operated valve 50 is provided in the outlet hose 51 that extends to the inhalator mask 52. The valve 50 includes a body 53 having an inlet passage 54 and an outlet passage 55 each of which extends to a central cylindrical opening 56. A valve member 57 which is cylindrical is retained in the opening 56 by a threaded member 58 and a circular handle 59 is provided for rotating the valve. The valve member includes an axial cavity 60, a first set of circumferentially spaced orifices 61 of varying diameters at the level of the inlet passage 54 and a second set of orifices 62 having the same diameter at the level of the outlet 55. A spring-loaded ball 63 is adapted to engage detents 64 in the underside of the handle 59 to selectively hold the valve member 57 in any particular position for aligning one of the orifices 61 with the inlet 54. By manipulating the handle 59, it is possible to bring one of the orifices corresponding to a certain amount of oxygen to be supplied into alignment with the inlet 54. Indicia in the form of a mark 65 and numbers 66 are provided on the body and handle respectively to indicate to the user the setting. In order to facilitate manipulating the manual valve 50, the body 53 preferably includes concave opposite side walls 67 that can be readily grasped between the thumb and fingers.

In operation, the user manipulates the handle 13 to turn the oxygen on and the oxygen passes from the valve 16 through the inlet passage 30 to the chamber 22 and thereafter through passage 31 to the chamber 23 and from there through the hose and valve 50 to the inhalation mask 52. The diaphragms 24, 25 function to successively reduce the pressure and maintain it at the proper pressure for use by the patient. In the event the pressure exceeds a predetermined amount, the valve 45 opens reducing the pressure in the chamber 22 so that the pressure in the chamber 23 is maintained at the required value.

In the event the patient requires a reduced amount of oxygen because of a particular physical condition, the valve 50 can be manipulated to select one of a plurality of predetermined settings.

I claim:

1. In an inhalation apparatus, the combination comprising
   an automatic pressure regulator including a body,
   said body having an opening for receiving a valve of an oxygen tank,
   said body having an outlet,
   said body including two chambers,
   a connecting passage extending from one chamber to the other,
   an inlet passage extending to one said chamber,
   each said chamber having a diaphragm closing one wall thereof,
   spring means yieldingly urging said diaphragm in one direction,
   an orifice associated with said inlet,
   an orifice associated with said passage,
   an orifice member for each said orifice,
   a lever for each said chamber,
   means for pivoting each said lever to its respective diaphragm,
   said lever having one end thereof pivotally connected to its respective diaphragm and the other end thereof engaging its respective orifice member,
   said means for pivoting said lever to its respective chamber comprising spaced groove shaped open recesses in said body,
   a pin extending through said lever and having its ends engaging said groove shaped recesses,
   and screw means threaded into said body and having a head removably engaging said pin and comprising the sole means for holding said pin in said recesses against movement out of said recesses.

2. In an inhalation apparatus, the combination comprising
   an automatic pressure regulator including a body,
   said body having an opening for receiving a valve of an oxygen tank,
   said body having an outlet,
   said body including two chambers,
   a connecting passage extending from one chamber to the other,
   an inlet passage extending to one said chamber,
   each said chamber having a diaphragm closing one wall thereof,
   spring means yieldingly urging said diaphragm in one direction,
   an orifice associated with said inlet,
   an orifice associated with said passage,
   an orifice member for each said orifice,
   a lever for each said chamber,
   means for pivoting each said lever to its respective diaphragm,
   said lever having one end thereof pivotally connected to its respective diaphragm and the other end thereof engaging its respective orifice member,
   a hose extending from said outlet and a manual valve attached to said hose,
   said valve including means for selectively varying in discrete increments the volume of oxygen passing through said hose to an inhaling mask on the end of said hose,
   said manual valve comprising a manual valve body,
   a valve member rotatably mounted in an opening in said manual valve body,
   said manual valve body having an inlet connected to one end of said hose and an outlet axially spaced with respect to said inlet,
   said valve body having an interior cavity extending between said inlet and said outlet,
   said valve member including a first set of orifices of different diameters circumferentially spaced about said valve member at the level of said inlet and extending from the periphery of said valve member to said interior cavity,
   said valve member having a second set of circumferentially spaced radially extending orifices extending from said cavity to the periphery of the valve member and in axially spaced relation to said first set of orifices at the level of said outlet,
   indicia means on said manual valve body,
   and a manually movable head on said valve member adapted to be engaged and rotated to bring selected orifices into alignment with said inlet and said outlet in order to vary the volume of oxygen passing through said manual valve body.

3. The regulator set forth in claim 2 including detent means on said manual valve body associated with said head for selectively holding the valve member in adjusted position.

4. The regulator set forth in claim 3 wherein said detent means comprises a spring-loaded ball.

5. The regulator set forth in claim 4 wherein said manual valve body includes concave sides for gripping the body with one hand to permit grasping the head of the valve member with the other.

6. The regulator set forth in claim 5 wherein said head is circular.

7. The regulator set forth in claim 6 including circumferentially spaced indicia on said head.

8. The regulator set forth in claim 2 wherein said means for pivoting said lever to its respective chamber comprises spaced groove shaped recesses in said body, a pin extending through said lever and engaging said groove shaped recesses, and screw means threaded into said body and having a head removably engaging said pin and comprising the sole means for holding said pin in said recesses against movement out of said recesses.

* * * * *

Disclaimer 4,243,155.—*Maurice M. Stewart,* West Bloomfield, Mich. VALVING AND AUTOMATIC PRESSURE REGULATOR FOR INHALATION APPARATUS. Patent dated Jan. 6, 1981. Disclaimer filed May 14, 1984, by the assignee, *Oxygen Therapy Institute, Inc.*

Hereby enters this disclaimer to all claims of said patent.

[*Official Gazette October 30, 1984.*]